(12) United States Patent
Morrison (10) Patent No.: US 8,960,189 B2
(45) Date of Patent: Feb. 24, 2015

(54) SYSTEM AND METHOD FOR MONITORING A METERED DOSE INHALER

(75) Inventor: Mark Steven Morrison, Basking Ridge, NJ (US)

(73) Assignee: Koninklijke Philips N.V., Eindhoven (NL)

( * ) Notice: Subject to any disclaimer, the term of this patent is extended or adjusted under 35 U.S.C. 154(b) by 787 days.

(21) Appl. No.: 13/131,100

(22) PCT Filed: Nov. 21, 2009

(86) PCT No.: PCT/IB2009/055256
§ 371 (c)(1),
(2), (4) Date: May 25, 2011

(87) PCT Pub. No.: WO2010/067240
PCT Pub. Date: Jun. 17, 2010

(65) Prior Publication Data
US 2011/0226237 A1 Sep. 22, 2011

Related U.S. Application Data

(60) Provisional application No. 61/121,580, filed on Dec. 11, 2008.

(51) Int. Cl.
*A61M 11/00* (2006.01)
*A61M 15/00* (2006.01)

(52) U.S. Cl.
CPC ........... *A61M 15/009* (2013.01); *A61M 15/008* (2014.02)
USPC .................................. 128/200.23

(58) Field of Classification Search
USPC ............ 128/200.14, 200.16, 200.23, 203.12, 128/203.15, 204.21, 204.22
See application file for complete search history.

(56) References Cited

U.S. PATENT DOCUMENTS

| | | | |
|---|---|---|---|
| 5,794,612 A | 8/1998 | Wachter et al. | |
| 6,152,130 A * | 11/2000 | Abrams et al. | 128/204.21 |
| 6,202,642 B1 * | 3/2001 | McKinnon et al. | 128/200.23 |
| 6,889,690 B2 * | 5/2005 | Crowder et al. | 128/203.15 |
| 7,066,029 B2 * | 6/2006 | Beavis et al. | 73/649 |
| 7,832,394 B2 * | 11/2010 | Schechter et al. | 128/200.24 |
| 2006/0150971 A1 * | 7/2006 | Lee et al. | 128/203.15 |

FOREIGN PATENT DOCUMENTS

| | | |
|---|---|---|
| EP | 1726322 A1 | 11/2006 |
| GB | 2013343 A | 8/1979 |
| WO | 02058771 A1 | 8/2002 |

* cited by examiner

*Primary Examiner* — Justine Yu
*Assistant Examiner* — Kathrynn Reilly (57) ABSTRACT

A system and method for dispensing metered doses of medicament to a subject that monitors one or more aspects of the dispensation. The medicament is aerosolized for dispensation to the subject so that the subject can inhale the medicament into his airway. The one or more aspects of the dispensation that are monitored based on ultrasonic energy generated by the aerosolization of the medicament. The one or more aspects of the dispensation that are monitored may include one or more of a number of doses dispensed, a number of doses remaining, whether any medicament remains to be dispensed, and/or other aspects of the dispensation of the medicament.

19 Claims, 5 Drawing Sheets

SYSTEM AND METHOD FOR MONITORING A METERED DOSE INHALER

This patent application claims the priority benefit under 35 U.S.C.§119(e) of U.S. Provisional Application No. 61/121,580 filed on Dec. 11, 2008, the contents of which are herein incorporated by reference.

This application is related to U.S. patent application Ser. No. 61/121,582, entitled "SYSTEM AND METHOD FOR MONITORING NEBULIZATION OF A MEDICAMENT," and filed Dec. 11, 2008, which is hereby incorporated into this application in its entirety.

The invention relates to monitoring one or more aspects of the dispensation of a medicament through a metered dose inhaler.

One known system for dispensing aerosolized medicament to subjects is the metered dose inhaler. Generally, metered dose inhalers dispense doses of medicament from a canister that holds the medicament with a propellant that aerosolizes the medicament dispensed from the canister. One of the drawbacks associated with metered dose inhalers is that subjects may not accurately monitor one or more aspects of the dispensation of the medicament. For example a subject may lose track of the number of doses that have been dispensed. As another example, a subject may not be able to tell with accuracy when all (or substantially) all of the medicament has been dispensed from a canister, and may continue to use the inhaler without actually receiving any medicament.

One aspect of the invention relates to a system configured to monitor treatment of a subject with a metered dose inhaler. In one embodiment, the system comprises a sensor and a processor. The sensor is configured to generate one or more output signals conveying information related to ultrasonic energy generated by a dispensation of a dose of medicament from an inhaler. The processor is configured to receive the one or more output signals generated by the sensor, and to monitor one or more aspects of the dispensation of the medicament based on the information related to the ultrasonic energy generated by the dispensation of the dose of medicament that is conveyed by the received one or more output signals.

Another aspect of the invention relates to a method of monitoring one or more aspects of treatment of a subject with a metered dose inhaler. In one embodiment, the method comprises generating one or more output signals conveying information related to ultrasonic energy generated by a dispensation of a dose of medicament from an inhaler; monitoring one or more aspects of the dispensation of the medicament based on the generated one or more output signals; and providing information to a recipient of the medicament related to the monitored one or more aspects of the dispensation of the medicament.

Yet another aspect of the invention relates to a system configured to monitor one or more aspects of treatment of a subject with a metered dose inhaler. In one embodiment, the system comprises means for generating one or more output signals conveying information related to ultrasonic energy generated by a dispensation of a dose of medicament; means for monitoring one or more aspects of the dispensation of the medicament based on the generated one or more output signals; and means for providing information to a recipient of the medicament related to the monitored one or more aspects of the dispensation of the medicament.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
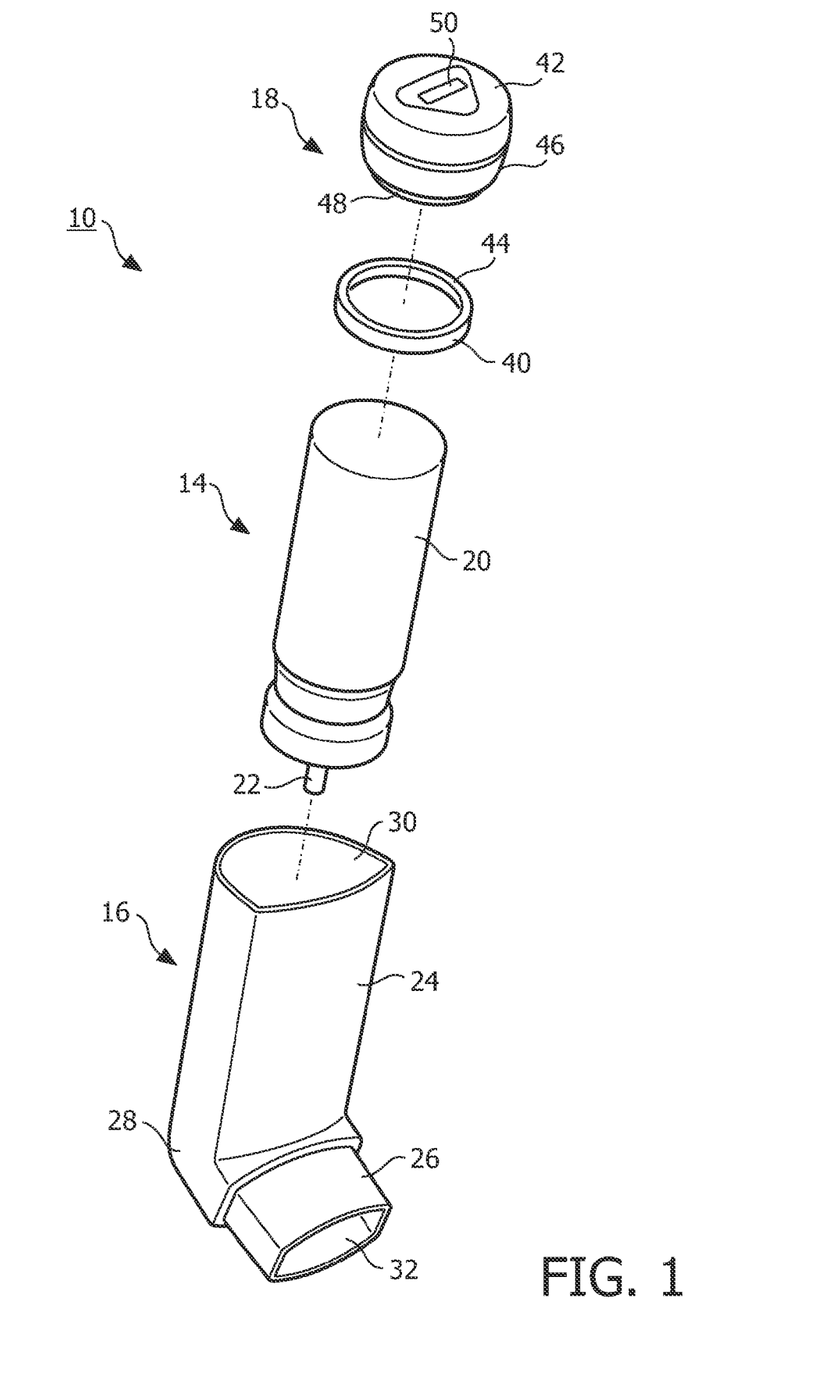
FIG. 1 illustrates a system configured to dispense metered doses of medicament to a subject, in accordance with one or more embodiments of the invention.

FIG. 1 illustrates a system 10 configured to dispense metered doses of medicament to a subject, according to one embodiment. System 10 aerosolizes the medicament for dispensation to the subject so that the subject can inhale the medicament into his airway. In one embodiment, system 10 monitors one or more aspects of the dispensation of the medicament. For example, system 10 may monitor a number of doses dispensed by system 10, a number of doses remaining within system 10, whether any medicament remains to be dispensed, and/or other aspects of the dispensation of the medicament. In one embodiment, system 10 comprises a medicament canister 14, an inhaler boot 16, and a dispensation monitor 18.

Medicament canister 14 holds the medicament, and dispenses metered doses of the medicament in aerosolized form. Medicament canister 14 includes a tank 20 and a stem 22. Tank 20 holds medicament, along with one or more other fluids. Stem 22 is hollow, and dispenses medicament from tank 20 if depressed inwardly to tank 20. Within tank 20, the medicament is held with at least an aerosol propellant (e.g., a CFC-type propellant, an HFA-type propellant, etc.). When canister 14 is actuated by the depression of stem 22, a metered quantity of pressurized liquid (including medicament and propellant) is allowed to escape through the opening in stem 22. As it escapes, the propellant in the pressurized liquid vaporizes (e.g., in 0.3 to 0.5 seconds), and the medicament that is carried by the propellant is dispersed into the surrounding gas cloud created by the vaporized propellant. The result is an aerosolized solution that includes particles of the medicament small enough to be inhaled. A solution formed with a CFC-type propellant may leave stem 22 at speeds between 60 and 90 miles per hour (HFA-type propellants may be a little slower).

Inhaler boot 16 holds canister 14, and guides aerosolized solution from canister 14 to the airway of the subject. Inhaler boot 16 includes a canister housing 24 and a mouthpiece 26. Typically, canister housing 24 and mouthpiece 26 is joined by an angled section 28. Within angled section 28, a canister seat is formed.

Canister housing 24 forms an opening 30 at an end opposite angled section 28, to enable canister 14 to be inserted therein. Opening 30, and the conduit formed by canister housing 24 is slightly larger than canister 14 to enable air to travel from opening 30 to mouthpiece 26 between canister 14 and the walls of canister housing 24.

Mouthpiece 26 forms an opening 32 at an end opposite angled section 28, and forms a conduit from canister seat 34 to opening 32. The exterior of mouthpiece 26 is adapted to be engaged by the mouth of the subject. The conduit formed by mouthpiece 26 is configured to carry aerosolized solution from within inhaler boot 16 into the airway of the subject (e.g., through the mouth of the subject).

Figure 2:
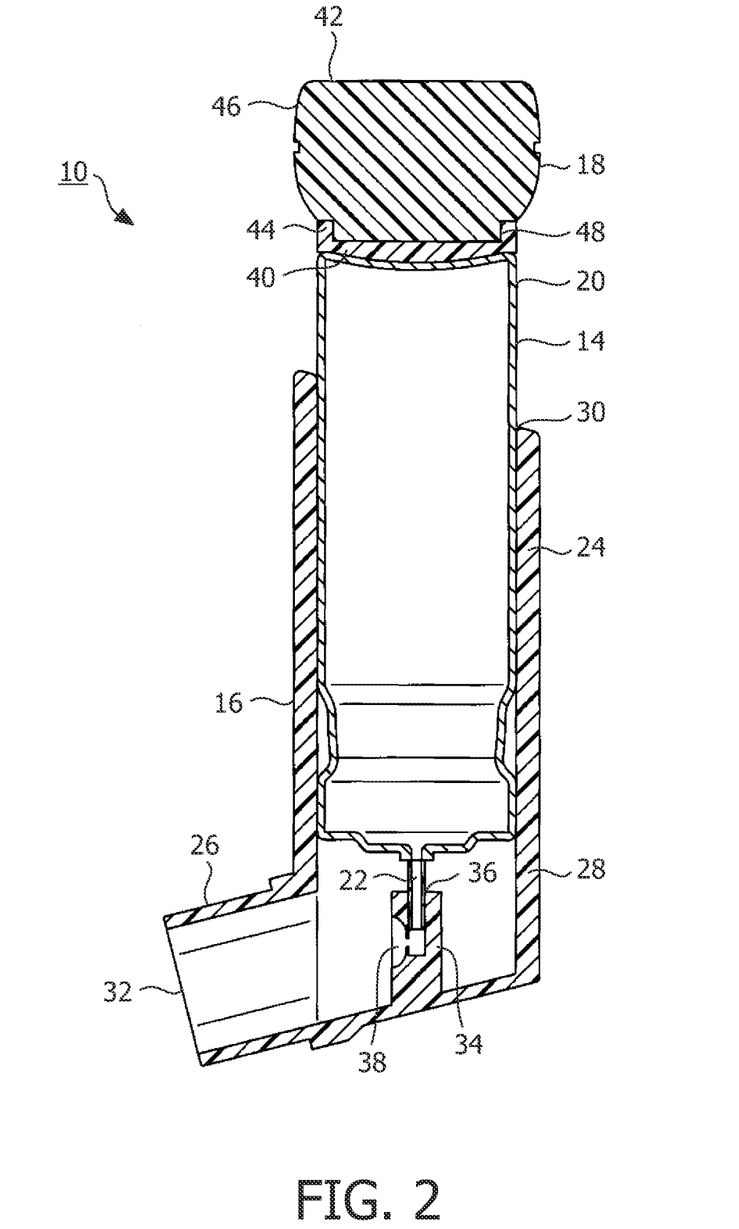
FIG. 2 illustrates a system configured to dispense metered doses of medicament to a subject, in accordance with one or more embodiments of the invention.

FIG. 2 illustrates of a cross-section of one embodiment of system 10 that shows the operation of system 10 in dispensing medicament. As can be seen in FIG. 2, a canister seat 34 disposed within angled section 28 of inhaler boot 16 forms a conduit from a stem opening 36 to a delivery opening 38. Canister seat 34 provides a seat that secures canister 14 in place within inhaler boot 16. In particular, stem opening 36 is configured to receive stem 22 of canister 14 to secure canister 14 with respect to inhaler boot 16. For example, in one embodiment, stem opening 36 is tapered so that as stem 22 is inserted into stem opening 36 a friction fit between the walls of stem opening 36 and stem 22 is achieved. The conduit between stem opening 36 and delivery opening 38 is configured to receive aerosolized solution from canister 14, and to guide the aerosolized solution as it is projected from canister 14 into mouthpiece 26.

During operation, stem 22 of canister 14 rests securely within stem opening 36 formed by canister seat 34 within inhaler boot 16. To dispense medicament from system 10 to the subject, the subject applies a force to canister 14 that moves tank 20 down into inhaler boot 16. This movement depresses stem 22 inwardly to tank 20. The depression of stem 22 into tank 20 releases a metered dose of propellant and medicament from canister 14 that becomes aerosolized and is guided from stem 22 into mouthpiece 26 of inhaler boot 16 by the conduit formed in canister seat 34 between stem opening 36 and delivery opening 38. The aerosolized solution is then drawn from the mouthpiece into the respiratory system of the subject as the subject inhales.

Referring back to FIG. 1, dispensation monitor 18 is configured to monitor one or more aspect of the dispensation of aerosolized medicament delivered by system 10 from canister 14. For example, dispensation monitor 18 may monitor a number of doses dispensed from canister 14, a number of doses remaining within canister 14, whether any medicament remains to be dispensed within canister 14, and/or other aspects of the dispensation of the medicament. Dispensation monitor 18 monitors the one or more aspects based on ultrasonic generated by the dispensation of the medicament.

In one embodiment, dispensation monitor 18 is removably secured to one or both of canister 14 and/or inhaler boot 16. In this embodiment, dispensation monitor 18 can be selectively removed from boot 16 and/or canister 14 and used with another canister and/or boot after canister 14 is exhausted. In one embodiment, dispensation monitor 18 is provided integrally with one or both of canister 14 and/or boot 16. As used herein, the term "provided integrally with" is intended to mean that dispensation monitor 18 is not intended for use with any other canister or boot than the one(s) that it is provided integrally with. In other words, removal of monitor 18 from a canister or boot with which it is integrally provided would likely render monitor 18 inoperable, and/or would destroy the mechanism by which monitor 18 was attached to the canister or boot.

In the embodiment illustrated in FIG. 1, dispensation monitor 18 is removably secured to canister 14, to enable dispensation monitor 18 to be implemented with a plurality of different canisters. In particular, the embodiment of dispensation monitor illustrated in FIG. 1 includes a base 40 and a body 42. Base 40 is attached on one side to canister 14. For example, base 40 may be adhered to canister 14 or even provided integrally with canister 14. On a side of base 40 opposite from canister 14, base 40 includes one or more features that selectively engage body 42 to hold body 42 on base 40. The one or more features that selectively engage body 42 shown in FIG. 1 is an annular ridge 44 that runs around the periphery of base 40. Body 42 includes a housing 46 that houses one or more of the components of dispensation monitor 18 described below. Housing 46 includes one or more features that are adapted to be selectively engaged by base 40. The one or more features of housing 46 adapted to be selectively engaged by base 40 shown in FIG. 1 include a groove 48 that is selectively engaged by annular ridge 44 formed on base 40. The selective engagement between annular ridge 44 and groove 48 may produce a snap-fit, a friction-fit, and/or some other selective engagement between base 40 and body 42. In one embodiment, annular ridge 44 is formed such that if body 42 is engaged with base 40 and then removed from base 40, annular ridge 44 becomes deformed. This would help to prevent body 42 from being re-attached to a base 40 coupled with a previously exhausted canister.

Figure 3:
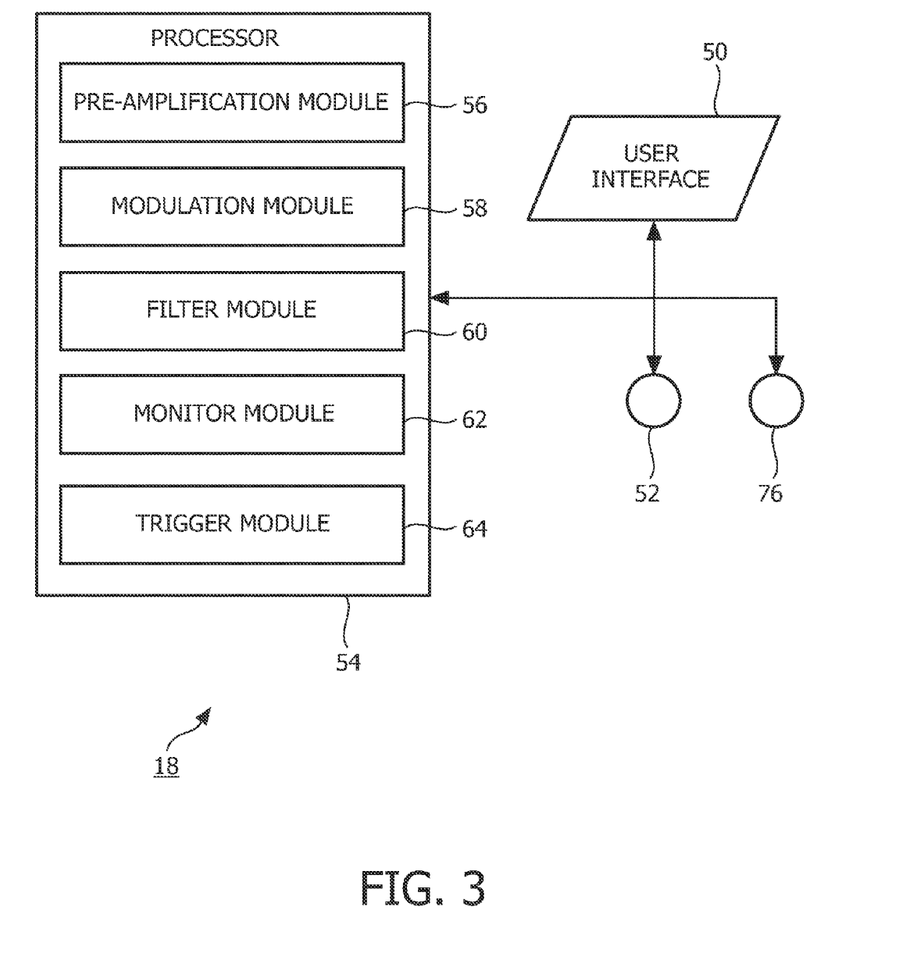
FIG. 3 illustrates a dispensation monitor that monitors one or more aspects of the dispensation of a medicament, in accordance with one or more embodiments of the invention.

FIG. 3 illustrates a functional block diagram of dispensation monitor 18. In the embodiment illustrated in FIG. 3, dispensation monitor 18 includes a user interface 50, a sensor 52, and a processor 54. It should be appreciated that this is for illustrative purposes only, as dispensation monitor 18 may, in some embodiments, include more or less components than are illustrated in the block diagram of FIG. 3.

User interface 50 is configured to provide an interface between dispensation monitor 18 and the subject through which the subject may receive information from dispensation monitor 18. This enables data, results, and/or instructions and any other communicable items, collectively referred to as "information," to be communicated between the subject and the components of dispensation monitor 18. In one embodiment, the form factor of dispensation monitor 18 is a consideration in the design of user interface 50. In this embodiment, the interface provided by user interface 50 may be relatively small and/or uncomplicated to limit the space that it takes up. Examples of interface devices suitable for inclusion in user interface 50 include a display screen, speakers, one or more indicator lights, an audible alarm, a numerical display, and/or other interface devices.

Sensor 52 is configured to generate one or more output signals conveying information related to ultrasonic energy generated by dispensation of a medicament (e.g., by system 10 shown in FIG. 1 and described above). As such, sensor 52 may include a transducer configured to convert ultrasonic energy to an electronic output signal (e.g., a current, a voltage, etc.). In one embodiment, sensor 52 includes an ultrasonic microphone (e.g., a microphone sensitive to frequencies higher than audible frequencies), a piezoelectric transducer, and/or other transducers capable of converting ultrasonic energy to an electronic output signal. In one embodiment, sensor 52 is an ultrasonic microphone that is pointed down into inhaler boot 16.

Operation of an inhaler (e.g., canister 14 and boot 16 shown in FIG. 1 and described above) to deliver aerosolized medicament to a subject generally generates ultrasonic energy. As such, the presence of this ultrasonic energy may be an indicator of a dispensation of an aerosolization and dispensation of a dose of medicament. In some cases, the ultrasonic energy generated by the dispensation of medicament may be modulated at a lower frequency (e.g., within the audible range) in a manner that is impacted by one or more aspects of the operation of the inhaler. For example, the presence of medicament within the inhaler, an amount of medicament present within the inhaler, an amount of medicament dispensed in a single dose, a type of medicament being dispensed (e.g., a composition of the medicament), and/or other aspects of the dispensation of medicament by the inhaler may impact the modulation of the ultrasonic energy generated by the dispensation of medicament. As such, in one embodiment, the information related to ultrasonic energy generated during the dispensation of medicament by the inhaler that is conveyed by the one or more output signals generated by sensor 52 enables detection of an ultrasonic carrier wave that can be monitored to determine one or more aspects of the dispensation of medicament from the inhaler. For example, the amplitude of the ultrasonic carrier wave may be modulated in a manner that provides an indication of when a dose of medicament has been administered, enables a determination as to whether any medicament remains in the inhaler, enables a determination of how much medicament (e.g., how many doses) remains in the inhaler, enables a determination of how much medicament has been dispensed in a single does, a type of medicament being dispensed (e.g., a composition of the medicament), and/or other aspects of the dispensation of medicament.

Processor 54 is configured to provide information processing capabilities in dispensation monitor 18. As such, processor 54 may include one or more of a digital processor, an analog processor, a digital circuit designed to process information, an analog circuit designed to process information, a state machine, and/or other mechanisms for electronically processing information. Although processor 54 is shown in FIG. 3 as a single entity, this is for illustrative purposes only. In some implementations, processor 54 may include a plurality of processing units. These processing units may be physically located within the same device, or processor 54 may represent processing functionality of a plurality of devices operating in coordination.

As is shown in FIG. 3, in one embodiment, processor 54 includes a pre-amplification module 56, a modulation module 58, a filter module 60, a monitor module 62, a trigger module 64, and/or other modules. Modules 56, 58, 60, 62, and/or 64 may be implemented in software; hardware; firmware; some combination of software, hardware, and/or firmware; and/or otherwise implemented. It should be appreciated that although modules 56, 58, 60, 62, and/or 64 are illustrated in FIG. 3 as being co-located within a single processing unit, in implementations in which processor 54 includes multiple processing units, modules 56, 58, 60, 62, and/or 64 may be located remotely from the other modules. Further, the description of the functionality of modules 56, 58, 60, 62, and/or 64 provided below is for illustrative purposes, and is not intended to be limiting, as any of modules 56, 58, 60, 62, and/or 64 may provide more or less functionality than is described. For example, one or more of modules 56, 58, 60, 62, and/or 64 may be eliminated, and some or all of its functionality may be provided by other ones of modules 56, 58, 60, 62, and/or 64. As another example, processor 54 may include one or more additional modules that perform some or all of the functionality attributed below to one of modules 56, 58, 60, 62, and/or 64.

Pre-amplification module 56 is configured to amplify the one or more output signals generated by sensor 52. In one embodiment, pre-amplification module 56 pre-amplifies the one or more output signals prior to subsequent processing by the modules of processor 54. The pre-amplification of the one or more output signals may facilitate the subsequent processing.

Modulation module 58 is configured to extract a modulated signal that is carried by an ultrasonic carrier signal detected from one or more of the output signals generated by sensor 52. In one embodiment, the modulated signal may include changes in amplitude of the ultrasonic carrier signal that convey information about the dispensation of medicament. For example, the modulated signal may include bursts of amplitude change and/or amplitude oscillations between about 1 kHz and about 10 kHz. In one embodiment, modulation module 58 comprises a rectifier that extracts the modulated signal from the ultrasonic carrier signal present in the one or more output signals generated by sensor 52.

Filter module 60 is configured to filter the modulated signal that is extracted by modulation module 60. In some instances, in addition to signals that convey information about dispensation of a medicament, the modulated signal may include noise and/or signals at frequencies that are not of interest. Filter module 60 may filter out frequencies of the modulated signal that interfere with the signal(s) that convey information about dispensation of a medicament. For example, in one embodiment, filter module 60 includes a band-pass filter with a range that includes at least some audible frequencies. The range of the band-pass filter may be, for instance, between about 2 kHz and about 10 kHz.

Monitor module 62 is configured to monitor dispensation of a medicament based on the filtered signal provided by filter module 60. As should be apparent from the foregoing, the filtered signal, which was originally carried in the ultrasonic energy generated by operation of an inhaler, conveys information related to whether medicament is being dispensed, an amount of medicament remaining in the inhaler, an amount of medicament dispensed in a single dose, a type of medicament being dispensed (e.g., a composition of the medicament), and/or other aspects of the dispensation of medicament, Monitor module 62 receives the filtered signal from filter module 60, and determines information related to one or more aspects of the dispensation of the medicament by the inhaler from the filtered signal. In one embodiment, monitor module 62 includes a frequency to voltage converter that converts the frequency information included within the filtered signal received from filter module 60 into voltage information. The voltage information is then monitored to determine information related to one or more aspects of the nebulization of the medicament by the nebulizer. In one embodiment, monitor module 62 then conveys information related to the one or more aspects of the dispensation of the medicament to a user via user interface 50.

Figure 4:
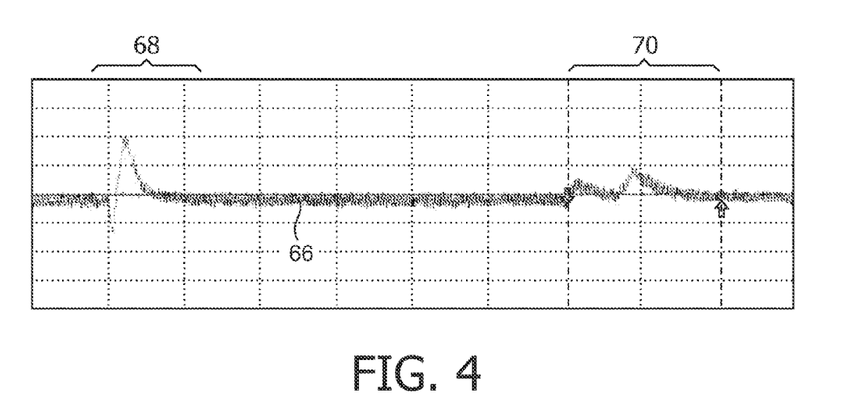
FIG. 4 illustrates a plot of a signal detected by an ultrasonic energy sensor during dispensations of medicament, according to one or more embodiments of the invention.

As was mentioned above, the ultrasonic energy generated by operation of an inhaler is modulated with a signal that varies in response to changes in one or more aspects of the operation of the inhaler. For example, FIG. 4 illustrates a plot of an amplitude of a signal 66 generated by a frequency-to-voltage conversion performed by the monitor module on the filtered signal received from the filter module as a function of time. During a first time period 68, spike in the amplitude of signal 66 indicates that a dose of a medicament has been dispensed. Signal 66 during first time period 68 is indicative of normal actuation of an inhaler to dispense a dose of medicament.

During a second time period 70, a smaller increase in the amplitude of signal 66 is present at two separate maxima within second time period 70. The amplitude of signal 66 during second time period 70 is indicative of a slow actuation of the inhaler, which changes the shape, duration, and/or intensity of signal 66 with respect to the shape, duration, and/or intensity of first time period 68. Similarly, the shape, duration, and/or intensity of signal 66 may be impacted by the amount of medicament left in the inhaler, the amount of medicament dispensed in a dose, a type of medicament being dispensed (e.g., a composition of the medicament), and/or other aspects of dispensation of medicament.

Returning to FIG. 3, in one embodiment, monitor module 62 detects dispensation of doses of medicament from the inhaler based on the signal received from filter module 60 in accordance with the principles discussed above with respect to FIG. 3. For example, in this embodiment, monitor module 62 may include a comparator that detects monitors a frequency-to-voltage conversion of the filtered signal that is provided to monitor module 62 from filter module 60 (e.g., a signal similar to the one illustrated in FIG. 4 and described above). As was set forth previously, the amplitude and/or shape of this signal indicates a dispensation of a dose of medicament from the inhaler. Indications of the detection performed by monitor module 62 may be provided to the user via user interface 50. For example, a number of doses that have been administered from a canister associated with the inhaler and/or a number of doses remaining within the canister may be provided to the user via user interface 50.

Although the detection of one or more aspects of medicament dispensation from ultrasonic energy generated during medicament dispensation may eliminate noise caused by various audible sound sources (as these sounds are not carried by ultrasonic carrier waves), certain environmental sources of ultrasonic energy still remain. For example, the noise that keys make when they collide generates ultrasonic energy similar to the energy generated by the dispensation of medicament from an inhaler. In order to avoid interference with determinations of one or more aspects of medicament dispensation by these extraneous sources of ultrasonic energy, monitor module 62 may provide additional analysis beyond threshold detection in identifying dispensations of medicament. In one embodiment, monitor module 62 analyzes the shape of the signal received from filter module 60, rather than merely comparing the amplitude of the signal to a threshold, in order to discriminate between dispensations of medicament and other sources of ultrasonic energy.

Figure 5:
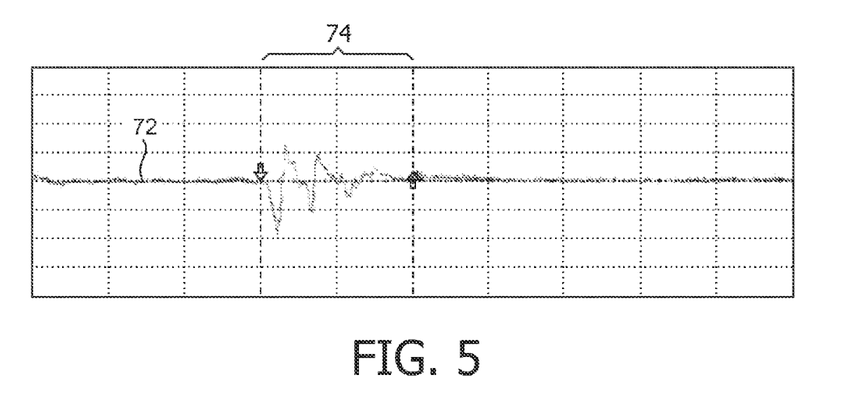
FIG. 5 illustrates a plot of a signal detected by an ultrasonic energy sensor caused by ambient noise, according to one or more embodiments of the invention.

By way of illustration, FIG. 5 shows a plot of an amplitude of a signal 72 generated by a frequency-to-voltage conversion performed by the monitor module on the filtered signal received from the filter module as a function of time. During a time period 74, a collision of keys on a key ring generates ultrasonic energy, which, after detection by sensors 52 and processing by modules 56, 58, and 60, results in the undulation in signal 72 shown in FIG. 5. As should be appreciated from a comparison of signal 72 in FIG. 5 with signal 66 in FIG. 4, the signal resulting from a collision of keys is more of an oscillation about a steady state level than the signal (shown in FIG. 4) resulting from a dispensation of medicament from an inhaler, which is more of an elevation of the signal from the steady state. However, a simple threshold detection (as described above) may not distinguish between the two signals. Another difference between variations in the amplitude of the signal caused by the dispensation of medicament and variations in the amplitude of the signal caused by a collision of keys or some similar implement, is that the variation in the signal caused by the collision of keys will take place over a relatively short period of time. In other words, period of time 74 shown in FIG. 5 will be significantly shorter than periods of time 68 and 70 shown in FIG. 4.

Returning to FIG. 3, in one embodiment, rather than analyzing a shape of the modulated signal carried in the ultrasonic energy detected by sensors 52, dispensation monitor 18 may include a trigger sensor 76 and trigger module 64. Trigger sensor 76 and trigger module 64 are configured to control operation of dispensation monitor 18 such that one or more aspects of the dispensation of medicament are monitored by monitor module 62 only at times when it is likely that medicament is being dispensed. As such, trigger sensor 76 and trigger module 64 form a trigger that triggers the operation of dispensation monitor 18.

Trigger sensor 76 may include one or more sensors that generate output signals indicating that a dispensation of medicament is likely. By way of non-limiting example, in one embodiment, trigger sensor 76 generates an output signal indicating whether the inhaler is being handled. For instance, trigger sensor 76 may include a touch sensor disposed on the canister of the inhaler, the boot of the inhaler, and/or dispensation monitor 18 at a location typically engaged by a user to actuate the inhaler to dispense a dose of medicament.

Trigger module 64 receives the output signal(s) generated by trigger sensor 76, and operates to selectively activate and deactivate the operation of modules 56, 58, 60, and/or 62 based on whether a dispensation of medicament is likely. For example, trigger sensor 76 and trigger module 64 may effectively act as a switch that enables one or more of modules 56, 58, 60, and/or 62 if a dispensation of medicament is likely.

Figure 6:
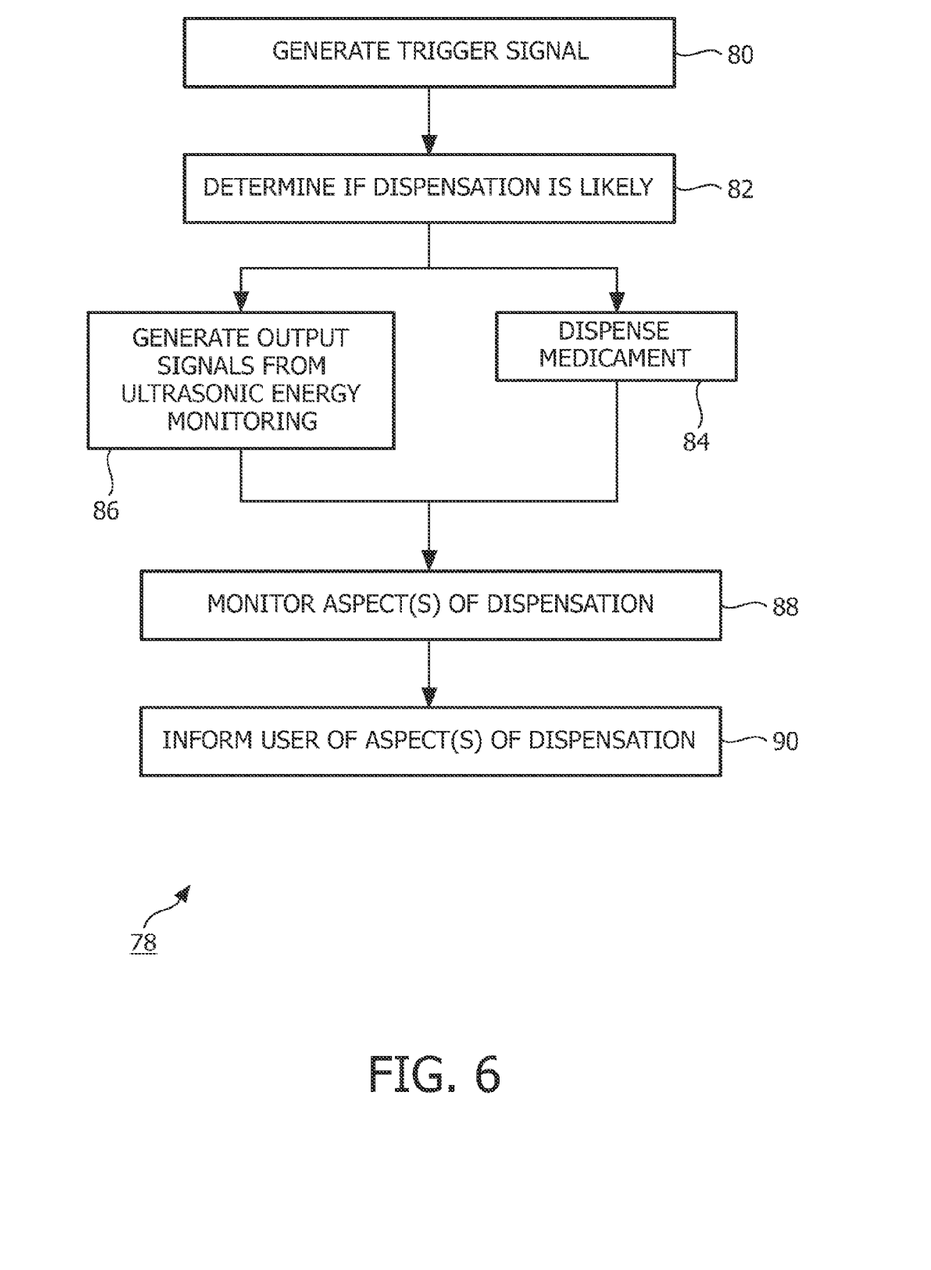
FIG. 6 illustrates a method of monitoring a dispensation of medicament to a subject, according to one or more embodiments of the invention.

FIG. 6 illustrates a method 78 of monitoring one or more aspects of dispensation of a medicament. The operations of method 78 presented below are intended to be illustrative. In some embodiments, method 78 may be accomplished with one or more additional operations not described, and/or without one or more of the operations discussed. Additionally, the order in which the operations of method 78 are illustrated in FIG. 6 and described below is not intended to be limiting. Although the implementation of method 78 are described within the context of the systems set forth above, in some embodiments, method 78 is implemented in one or more other contexts.

Method 78 includes an operation 80, at which an output signal is generated that indicates whether a dispensation of a medicament from an inhaler is likely. For example, the output signal may indicate whether a trigger is engaged. In one embodiment, operation 80 is performed by a trigger sensor that is similar to or the same as trigger sensor 76 (shown in FIG. 3 and described above).

At an operation 82, a determination is made as to whether the output signal generated at operation 80 indicates that a dispensation of a medicament from the inhaler is likely. In one embodiment, operation 82 is performed by a trigger module that is similar to or the same as trigger module 64 (shown in FIG. 3 and described above). If it is determined that a dispensation of medicament is not likely, then method 78 returns to operation 80. If it is determined at operation 82 that a dispensation of medicament is likely, then method 78 proceeds to an operation 84.

At operation 84, a dose of medicament is dispensed. Operation 84 includes aerosolizing the medicament for dispensation. In one embodiment, operation 84 is performed by an inhaler including a canister and boot that are the same as or similar to canister 14 and boot 16 (shown in FIG. 1 and described above).

At an operation 86, one or more output signals are generated that convey information related to ultrasonic energy generated by the dispensation of the medicament. In one embodiment, operation 86 is performed by a sensor that is the same as or similar to sensor 52 (shown in FIG. 3 and described above).

At an operation 88, one or more aspects of the dispensation of the medicament are monitored based on the generated one or more output signals. In one embodiment, operation 88 is performed by a processor that is the same as or similar to processor 54 (shown in FIG. 3 and described above).

At an operation 90, information related to the monitored one or more aspects of the dispensation of medicament are provided to a recipient of the medicament. In one embodiment, operation 90 is performed by a user interface that is the same as or similar to user interface 50 (shown in FIG. 3 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system configured to monitor treatment of a subject with a metered dose inhaler, the system comprising
a sensor configured to generate one or more output signals conveying information related to ultrasonic energy generated by a dispensation of a dose of medicament from an inhaler; and
a processor configured to receive the one or more output signals generated by the sensor, and to monitor one or more aspects of the dispensation of the medicament based on the information related to the ultrasonic energy generated by the dispensation of the dose of medicament that is conveyed by the one or more output signals,
wherein the ultrasonic energy generated by the dispensation of the dose of medicament comprises an ultrasonic carrier signal modulated at a modulation frequency and wherein the information conveyed by the one or more output signals generated by the sensor enables detection of the ultrasonic carrier signal by the processor, and
wherein the information on which the one or more aspects of the dispensation of the medicament is based includes the modulation frequency, and
wherein monitoring of the one or more aspects of the dispensation of the medicament by the processor comprises one or more of monitoring whether a portion of the medicament remains to be dispensed, monitoring a number of doses of the medicament remaining in the inhaler, or counting a number of doses of the medicament that have been dispensed from the inhaler.

2. The system of claim 1, wherein the modulation frequency is between about 1 kHz and about 10 kHz.

3. The system of claim 1, wherein the processor is configured to monitor the one or more aspects of the dispensation of the medicament based on the ultrasonic carrier signal modulated at the modulation frequency.

4. The system of claim 1, wherein the sensor comprises an ultrasonic microphone.

5. The system of claim 1, further comprising an inhaler boot carrying the sensor.

6. The system of claim 1, further comprising an inhaler canister carrying the sensor.

7. The system of claim 1, further comprising a user interface that provides a user with information related to the one or more aspects of the dispensation of medicament that are monitored by the processor.

8. The system of claim 1, further comprising a trigger configured to control operation of the processor such that if the trigger is engaged the processor monitors the one or more aspects of the dispensation of the medicament, and if the trigger is not engaged the processor pauses monitoring the one or more aspects of the dispensation of the medicament.

9. A method of monitoring one or more aspects of treatment of a subject with a metered dose inhaler, the method comprising steps of:
generating one or more output signals conveying information related to ultrasonic energy generated by a dispensation of a dose of medicament from an inhaler;
monitoring one or more aspects of the dispensation of the medicament based on the one or more output signals;
providing information to a recipient of the medicament related to the one or more aspects of the dispensation of the medicament;
wherein the ultrasonic energy generated by the dispensation of the dose of medicament comprises an ultrasonic carrier signal modulated at a modulation frequency and wherein the information conveyed by the generated one or more output signals enables detection of the ultrasonic carrier signal by the processor, and
wherein the information on which the one or more aspects of the dispensation of the medicament is based includes the modulation frequency, and
wherein monitoring of the one or more aspects of the dispensation of the medicament by the processor comprises one or more of monitoring whether a portion of the medicament remains to be dispensed, monitoring a number of doses of the medicament remaining in the inhaler, or counting a number of doses of the medicament that have been dispensed from the inhaler.

10. The method of claim 9, wherein the modulated frequency is between about 1 kHz and about 10 kHz.

11. The method of claim 9, wherein the one or more aspects of the dispensation of the medicament are monitored based on the ultrasonic carrier signal modulated at the modulation frequency.

12. The method of claim 9, further comprising aerosolizing a metered dose of medicament with the inhaler.

13. The method of claim 9, further comprising determining whether a trigger is engaged, wherein the trigger controls the monitoring of the one or more aspects of the dispensation of the medicament such that if the trigger is determined to be engaged the one or more aspects of the dispensation of the medicament are monitored based on the one or more output signals, and if the trigger is determined to not be engaged the one or more aspects of the dispensation of the medicament are not monitored based on the generated one or more output signals.

14. A system configured to monitor one or more aspects of treatment of a subject with a metered dose inhaler, the system comprising
means for generating one or more output signals conveying information related to ultrasonic energy generated by a dispensation of a dose of medicament;
means for monitoring one or more aspects of the dispensation of tile medicament based on the one or more output signals;
means for providing information to a recipient of the medicament related to the one or more aspects of the dispensation of the medicament;
wherein the ultrasonic energy generated by the dispensation of the dose of medicament comprises an ultrasonic carrier signal modulated at a modulation frequency and wherein the information conveyed by the one or more output signals enables detection of the ultrasonic carrier signal by the processor, and wherein the information on which the one or more aspects of the dispensation of the medicament is based includes the modulation frequency, and wherein monitoring of the one or more aspects of the dispensation of the medicament by the processor comprises one or more of monitoring whether a portion of the medicament remains to be dispensed, monitoring a number of doses of the medicament remaining in the inhaler, or counting a number of doses of the medicament that have been dispensed from the inhaler.

15. The system of claim 14, wherein the modulation frequency is between about 1 kHz and about 10 kHz.

16. The system of claim 14, wherein the one or more aspects of the dispensation of the medicament are monitored based on the ultrasonic carrier signal modulated at the modulation frequency.

17. The system of claim 14, wherein the means for monitoring the one or more aspects of the dispensation of the medicament comprises one or more of means for monitoring whether a portion of the medicament remains to be dispensed, monitoring a number of doses of the medicament remaining in the inhaler, or means for counting a number of doses of the medicament that have been dispensed.

18. The system of claim 14, further comprising means for aerosolizing a metered dose of medicament.

19. The system of claim 14, further comprising means for controlling the means for monitoring of the one or more aspects of the dispensation of the medicament such that if the means for controlling are determined to be engaged the one or more aspects of the dispensation of the medicament are monitored based on the one or more output signals, and if the means for controlling are determined to not be engaged the one or more aspects of the dispensation of the medicament are not monitored based on generated the output signals.

* * * * *